United States Patent
Balandras et al.

(10) Patent No.: US 8,685,933 B2
(45) Date of Patent: Apr. 1, 2014

(54) CASEIN-DERIVED PEPTIDES HAVING ANXIOLYTIC ACTIVITY

(75) Inventors: Frederique Balandras, Nancy (FR);
Laurent Miclo, Villers-les-Nancy (FR);
Jean-Luc Gaillard, Luc sur Mer (FR);
Yves Le Roux, Vandoeuvre-les-Nancy (FR); Francois Laurent, Jarville (FR)

(73) Assignee: Universite de Lorraine, Nancy Cedex (FR)

( * ) Notice: Subject to any disclaimer, the term of this patent is extended or adjusted under 35 U.S.C. 154(b) by 952 days.

(21) Appl. No.: 12/519,017

(22) PCT Filed: Dec. 13, 2007

(86) PCT No.: PCT/EP2007/063863
§ 371 (c)(1), (2), (4) Date: Nov. 5, 2009

(87) PCT Pub. No.: WO2008/071755
PCT Pub. Date: Jun. 19, 2008

(65) Prior Publication Data
US 2010/0130433 A1 May 27, 2010

(30) Foreign Application Priority Data

Dec. 13, 2006 (FR) ..................... 06 10855

(51) Int. Cl.
*A61K 38/08* (2006.01)
*A61K 47/42* (2006.01)
*A23J 3/10* (2006.01)

(52) U.S. Cl.
USPC .......... 514/21.7; 530/328; 530/329; 530/360; 514/775

(58) Field of Classification Search
None
See application file for complete search history.

(56) References Cited

U.S. PATENT DOCUMENTS 5,846,939 A * 12/1998 Miclo et al. ............. 514/17.5

FOREIGN PATENT DOCUMENTS

| EP | 0 714 910 | 6/1996 |
| EP | 0714910 A1 | 6/1996 |
| EP | 1 188 767 | 3/2002 |
| FR | 0 714 910 | * 6/1994 |

OTHER PUBLICATIONS

Lecouvey, 1997, Eur. J. Biochem., 248, 872-878.*
Michaelidou, 1998, J Dairy Sci., 81, 3109-3116.*
Maruyama et al., "A peptide inhibitor of angiotensin I converting enzyme in the tryptichydrolysate of casein," Agric. Biol. Chem., (1982) 46(5):1393-1394.

Frochot "Étude d'undécapeptide à activité de type benzodiazépine issu d'une protéine du lait bovin," (1998) Thèse de l'Institut Polytechnique de Lorraine (INPL) (with English translation) 205 pp.
Thomson "Recent Developments in Protein Recovery and Purification," J Chem Tech Biotechnol (1984) 34B:190-198.
Lecouvey, M., et al., Two-Dimensional H-NMR and CD Structural Analysis in a Micellar Medium of a Bovine Alphasi-Casein Fragment Having Benzodiazepine-Like Properties, European Journal of Biochemistry, Sep. 1997;248(3):872-78.
Guesdon, B., et al., A tryptic hydrolysate from bovine milk alpha-s1-casein improves sleep in rats subjected to chronic mild stress, Peptides, Jun. 2006;27(6):1476-82.
Miclo, L., et al., Characterization of alpha-casozepine, a tryptic peptide from bovine alphas1-casein with benzodiazepine-like activity, FASEB Journal, Aug. 2001;15(10):1780-92.
Michaelidou, A., et al., Isolation and identification of some major water-soluble peptides in feta cheese, J. Dairy Sci., 1998;81:3109-16.
Zioudrou, C., et al., 1979, Opioid peptides derived from food proteins: the exorphins, J Biol Chem. Apr. 10, 1979;254(7):2446-9.
Cakir-Kiefer et al., "In Vitro Digestibility of α-Casozepine, a Benzodiazepine-like Peptide from Bovine Casein, and Biological Activity of Its Main Proteolytic Fragment," Journal of Agricultural and Food Chemistry (2011) pp. A-I.
Mercier et al., "Structure primaire de la caséine αs1 bovine Séquence complète," Eur. J. Biochem. (1971) 23:41-51.
Nagao et al., "Isolation and sequence analysis of bovine αs1-casein cDNA clone," (1984) Agric. Biol. Chem., 48(6): 1663-1667.
Zioudrou et al., "Opioid peptides derived from food proteins: the exorphins," (1979) J. Biol. Chem. 254(7):2446-2449.
Loukas et al., "Opiod activities and structures of α-casein-derived exorphins," Biochemistry (1983) 22:4567-4573.
Pellow et al., "Validation of open:closed arm entries in an elevated plus-maze as a measure of anxiety in the rat," (1985) J. Neurosci. Methods, 14(3):149-167.
Maruyama et al., "Angiotensin I-converting enzyme inhibitory activity of the C-terminal hexapeptide of αs1-casein," Agric. Biol. Chem. (1987) 51(9):2557-2561.
Bourin et al., "The mouse light/dark box test," Eur. J. Pharmacol. (2003) 463(1-3):55-65.
Miclo et al., "Characterization of α-casozepine, a tryptic peptide from bovine αs1-casein with benzodiazepine-like activity," FASEB J. (2001) 15:1780-1782.
LeCouvey et al., "Two dimentional 1H-NMR and CD structural analysis in a micellar medium of a bovin αs1-casein fragment having benzodiazepine-like properties," (1997) Eur. J. Biochem. 248:872-878.
Maubois "Separation, extraction and fractionation of milk protein components," Le Lait (1984) 64:485-495.

(Continued)

*Primary Examiner* — Satyanarayana R Gudibande
(74) *Attorney, Agent, or Firm* — Pepper Hamilton LLP

(57) ABSTRACT

The invention relates to peptides and, in particular, heptapeptides derived from milk casein $\alpha_{s1}$ and having anxiolytic activity. The invention also relates to pharmaceutical and food compositions containing said peptides and to the preparation methods thereof.

6 Claims, 3 Drawing Sheets

(56) References Cited

OTHER PUBLICATIONS

Figure 1:
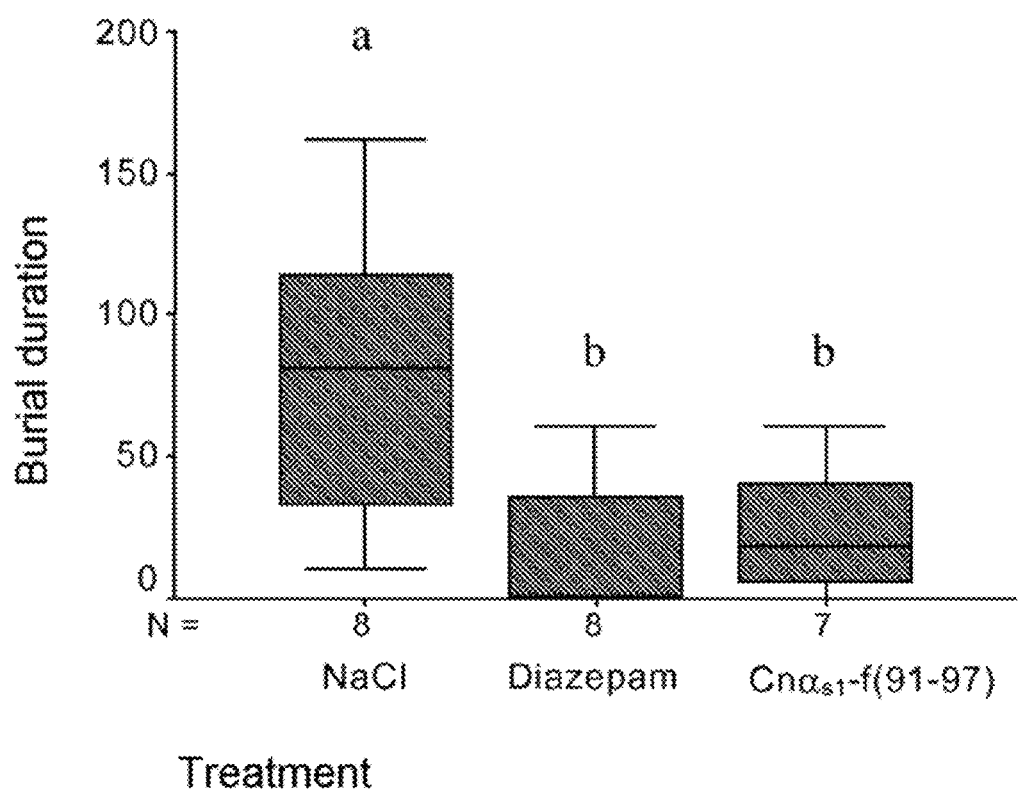

Sanogo et al., "Purification of αs1-casein by Fast Protein Liquid Chromatography," J. Dairy Sci. (1989) 72:2242-2246.

Merrifield "Solid phase peptide synthesis. I. Synthesis of a tetrapeptide," J. Am. Chem. Soc. (1963) 85:2149-2154.

Pinel et al., "Burying as a defensive response in rats," J. Comp. Physiol. Psychol. (1978) 92:708-712.

* cited by examiner

SEQUENCE LISTING

```
<160> NUMBER OF SEQ ID NOS: 3

<210> SEQ ID NO 1
<211> LENGTH: 7
<212> TYPE: PRT
<213> ORGANISM: Bos taurus

<400> SEQUENCE: 1

Tyr Leu Gly Tyr Leu Glu Gln
1               5

<210> SEQ ID NO 2
<211> LENGTH: 8
```

```
<212> TYPE: PRT
<213> ORGANISM: Bos taurus

<400> SEQUENCE: 2

Tyr Leu Gly Tyr Leu Glu Gln Leu
1               5

<210> SEQ ID NO 3
<211> LENGTH: 9
<212> TYPE: PRT
<213> ORGANISM: Bos taurus

<400> SEQUENCE: 3

Tyr Leu Gly Tyr Leu Glu Gln Leu Leu
1               5
```

CASEIN-DERIVED PEPTIDES HAVING ANXIOLYTIC ACTIVITY

CROSS-REFERENCE TO RELATED APPLICATIONS

This application is the U.S. National Stage filing under 35 U.S.C. §371 of International Application Serial No. PCT/EP2007/063863 filed Dec. 13, 2007, which claims priority under 35 U.S.C. §119(a) to French Application Serial No. 06/10855 filed Dec. 13, 2006, each of which is incorporated herein by reference in its entirety.

The present invention relates to peptides derived from casein $\alpha_{s1}$ with anxiolytic activity as well as to pharmaceutical compositions and food compositions comprising these peptides.

Casein by various fractionation techniques gives the main fractions which are respectively designated as: casein κ, casein β, casein $\alpha_{s1}$ and casein $\alpha_{s2}$. The amino acid sequences of these caseins are well-known, in particular that of casein $\alpha_{s1}$ was determined by MERCIER et al. (1) and NAGAO et al. (2).

It was shown that certain peptide fragments of these different caseins have various biological activities and notably opiate or anti-opiate activities and angiotensin I conversion enzyme inhibitory activities. Thus, the peptides 90-96 and 90-95 of casein $\alpha_{s1}$ have a distinct opiate activity [ZIOUDROU et al. (3) and LOUKAS et al. (4)]. The peptides 23-64 and 194-199, as for them, are inhibitors of the angiotensin I conversion enzyme [MARUYAMA and SUZUKI (5) and MARUYAMA et al. (6).

A peptide having an original activity of the anxiolytic type was detected in trypsic hydrolysate of $\alpha_{s1}$ casein [EP 0714910 (7)]. It corresponds to the fragment 91-100 and was designated as α-casozepine [MICLO et al. (8)]. The structure of this decapeptide was investigated by two-dimensional $^1$H-NMR. The sequence comprised between the glycine 93 and leucine 99 residues adopts in a micellar medium a helix $3_{10}$ structure initiated and terminated by a α helix turn. The lateral chains of the hydrophobic residues are located on the same face of the helix while the lateral chains of the hydrophilic residues are located on the other face, which imparts an amphiphilic character to the peptide and which may allow it to interact with the membranes. The ionic interactions between the guanidinium group of the arginine 100 residue and the carboxylic groups of the glutamic acid 96 and arginine 100 residues show the fundamental role of the carboxy-terminal arginine residue in the stabilization of the helicoidal structure. In such a structure, the aromatic rings of both tyrosine residues in positions 91 and 94 are oriented in such a way that the distance between their centers (0.56 nm on average) is comparable with the distance observed between the centers of aromatic rings of nitrazepam, a benzodiazepine known for its anxiolytic properties ([LECOUVEY et al. (9). The substitution of the arginine 100 residue with an alanine residue strongly reduces the helicity of the decapeptide and the result is a reduction in the affinity of this peptide for the benzodiazepine site of the $GABA_A$ receptor by a factor of 300,000 [Thesis of Céline Frochot, (10)]. This decapeptide, after oral absorption, may undergo proteolytic attacks by the enzymes of digestive tract which may reduce its bioavailability and therefore prevent it from reaching its biological target. Now, it is well known that for small peptides, absorption of enterocytes is more effective than that of larger fragments and that their resistance towards digestive proteases is increased. Thus, among the fragments generated during the digestion of the decapeptide, some may be more absorbable and more resistant, but with view to the structural data from the decapeptide, without being able to retain the least activity of anxiolytic type.

Surprisingly, certain peptides derived from the decapeptide and not containing the arginin 100 key residue exhibit anxiolytic properties in behavioral tests in vivo in rats. Considering their small size, these peptides are more easily absorbable and less easily degradable.

Listing of the Sequences

SEQ ID NO. 1: Heptapeptide corresponding to the positions 91-97 of $\alpha_{s1}$ casein SEQ ID NO. 2: Octapeptide corresponding to the positions 91-98 of $\alpha_{s1}$ casein SEQ ID NO. 3: Nonapeptide corresponding to the positions 91-99 of $\alpha_{s1}$ casein

DESCRIPTION OF THE INVENTION

The present invention relates to isolated peptides having one of the sequences SEQ ID NOs. 1-3.

The invention also relates to polynucleotides coding for the peptides of SEQ ID NOs. 1-3.

Another object of the invention is a host organism excluding humans, expressing a peptide according to any of SEQ ID NOs. 1-3.

Finally, the invention also relates to an enzymatic hydrolysate of casein comprising a peptide according to the invention.

In another aspect, the invention relates to peptides according to SEQ ID NOs. 1-3 and to enzymatic hydrolysates of the casein according to the invention for therapy, preferably, for treating anxiety, sleep disorders and epilepsy.

The invention also relates to pharmaceutical compositions containing as an active ingredient, an effective amount of a peptide according to the invention and/or an effective amount of a hydrolysate according to the invention in combination with a suitable pharmaceutical carrier.

The invention also relates to the use of a peptide according to the invention and/or a hydrolysate according to the invention for obtaining a drug intended to treat anxiety, sleep disorders and epilepsy.

Another object of the present invention is a food composition containing an effective amount of a peptide according to the invention and/or an effective amount of a hydrolysate according to the invention.

The invention also relates to a food supplement containing an effective amount of a peptide according to the invention and/or an effective amount of a hydrolysate according to the invention in combination with alimentary supports of protein or carbohydrate nature.

Another object of the present invention is a method for preparing peptides having anxiolytic activity characterized in that it comprises the following steps:
  enzymatic hydrolysis of casein,
  isolation of at least one peptide selected from the peptides having the SEQ ID NOs. 1-3.

Thus, the present invention relates to peptides derived from $\alpha_{s1}$ casein, the sequence of which is illustrated in SEQ ID NOs. 1-3. The invention therefore relates to peptides for which the amino acid sequence is selected from: Tyr-Leu-Gly-Tyr-Leu-Glu-Gln (SEQ. ID NO. 1), Tyr-Leu-Gly-Tyr-Leu-Glu-Gln-Leu (SEQ. ID NO. 2) and Tyr-Leu-Gly-Tyr-Leu-Gln-Leu-Leu (SEQ. ID NO. 3). In a preferred embodiment, the invention relates to the heptapeptide of sequence SEQ ID NO. 1 with the amino acid sequence Tyr-Leu-Gly-Tyr-Leu-Glu-Gln.

The invention also relates to modified peptides having one of the SEQ ID NOs. 1-3 and retaining their anxiolytic properties. The invention also relates to fusion proteins or to recombinant proteins comprising the peptides according to the invention.

In a second aspect, the invention relates to polynucleotides coding for the peptides according to the invention. Because of the degeneration of the genetic code, different polynucleotides may code for a second peptide. According to the present invention, by "polynucleotide" is meant a single strand nucleotide chain or its complementary which may be of the DNA or RNA type, or a double strand nucleotide chain which may be of the (complementary) or genomic cDNA type. Preferably, the polynucleotides of the invention are of the DNA, notably double strand DNA, type. The term of "polynucleotide" also designates modified polynucleotides. Preferably the polynucleotides of the present invention may be prepared by standard molecular biology techniques such as those described by Sambrook et al. (Molecular Cloning: A Laboratory Manual, 1989) or by chemical synthesis.

Another object of the invention is a host organism expressing a peptide according to any of SEQ ID NOs. 1-3. The peptides of the present invention may be expressed and produced in different host organisms according to techniques well-known to one skilled in the art. Typically, the host organism is transformed with an expression cassette comprising a polynucleotide coding for a peptide according to the invention. This polynucleotide may be integrated into the genome of the host organism or be replicated in the host organism in a stable way. By host organism, in particular, is meant according to the invention, any lower or higher mono- or pluricellular organism, in particular selected from bacteria, yeasts, fungi, and mammals. By host organism is meant a non-human organism. The peptides of the invention may therefore be produced and isolated or purified from transformed host organisms expressing them.

Preferably the peptides according to the invention are obtained from milk casein and more preferentially from $\alpha_{s1}$ casein. The casein used is preferentially casein from bovine milk and more preferentially from dairy cows (*Bos Taurus*). The sequence of $\alpha_{s1}$ casein is referenced in the Swiss Prot database under the number P02662. After fractionation of the milk proteins, the casein is "digested" or hydrolyzed with suitable enzymes in order to obtain the peptides according to the invention. In a first embodiment, the milk casein is directly hydrolyzed with enzymes in order to obtain the desired peptides. In this embodiment, it may be necessary to partially or totally purify the peptides according to the invention after hydrolysis. In a second embodiment according to the invention, enzymatic hydrolysis is directly carried out on $\alpha_{s1}$ casein. In this embodiment, the obtained hydrolysate will already be enriched with peptides according to the invention and additional purification steps will often not be necessary. One skilled in the art will select the suitable enzymes for obtaining the desired peptides. These techniques are well-known to one skilled in the art and described in the literature. The object of the invention is therefore also a hydrolysate of casein comprising a peptide according to the invention. Preferably, this is a hydrolysate of $\alpha_{s1}$ casein.

The peptides of the present invention have an anxiolytic effect. The invention relates to the use of the peptides notably for treating anxiety, sleep disorders, epilepsy.

The invention therefore also relates to peptides according to SEQ ID NOs. 1-3 and to enzymatic hydrolysates of $\alpha_{s1}$ casein according to the invention for treating anxiety, sleep disorders and epilepsy.

The invention also relates to pharmaceutical compositions containing as an active ingredient, an effective amount of a peptide according to the invention and/or an effective amount of a hydrolysate according to the invention in combination with a suitable pharmaceutical carrier.

These compositions may be formulated for administration to mammals, including humans. The dosage varies depending on the treatment and depending on the relevant affection. These compositions are made so as to be able to be administered via the digestive or parenteral route.

In the pharmaceutical compositions of the present invention for oral, sublingual, sub-cutaneous, intramuscular, intravenous, transdermal, local or rectal administration, the active ingredient may be administered as administration unit forms, in a mixture with conventional pharmaceutical carriers, to animals and to human beings. The suitable administration unit forms comprise oral forms such as tablets, gelatin capsules, powders, granules and oral solutions or suspensions, the sublingual and buccal administration forms, the subcutaneous, intramuscular, intravenous, intranasal, or intraocular administration forms and the rectal administration forms.

When a solid composition is prepared in the form of tablets, the main active ingredient is mixed with a pharmaceutical carrier such as gelatin, starch, lactose, magnesium stearate, talc, acacia gum or the like. The tablets may be coated with saccharose or other suitable materials or they may further be treated in such a way that they have a prolonged or delayed activity and they continuously release a predetermined amount of active ingredient.

A gelatin capsule preparation is obtained by mixing the active ingredient with a diluent and by pouring the obtained mixture in soft or hard gelatin capsules.

A preparation as a syrup or elixir may contain the active ingredient together with a sweetener, an antiseptic, as well as an agent giving taste and a suitable coloring agent.

The granules dispersible in water may contain the active ingredient as a mixture with dispersion agents or wetting agents, or suspension agents, as well as with taste-correcting agents or sweeteners.

The peptides and hydrolysates according to the invention may be used in therapy alone or as a combination with at least one other active agent. These other active agents are in particular selected from suitable active agents for treating anxiety, sleep disorders and epilepsy. These may be adjuvants with which the activity of the compounds according to the invention may be improved, or further other active agents known for their use in the treatment of said affections. Such active agents are well known to one skilled in the art, are available commercially or further described in reference text books such as the "Dictionnaire Vidal", edited with updates every year.

The present invention therefore also relates to a product comprising a compound according to the invention and another active agent as a combination product for simultaneous separate use or a use spread out over time in therapy, and in particular in the treatment of anxiety and sleep disorders. These other active agents are in particular selected from suitable active agents for treating anxiety such as for example the compounds from the class of benzodiazepines or the inhibitors of serotonin recapture.

The invention also relates to the use of a peptide according to the invention and/or a hydrolysate according to the invention for obtaining a drug intended for treating anxiety, sleep disorders and epilepsy.

Another object of the present invention is a food composition containing an effective amount of a peptide according to the invention and/or an effective amount of a hydrolysate according to the invention. By food composition is meant all which is able to be used as food. The peptides may be used as an active ingredient either in food compositions in combination with alimentary supports of protein or carbohydrate nature, or in food products intended for special feeding. The peptides or hydrolysates according to the invention may also be administered as food supplements. These food supplements are suitable for supplementing the food of persons notably subject to anxiety, sleep disorders and epilepsy.

The invention also relates to methods for obtaining peptides and hydrolysates according to the invention. Full casein is obtained from milk by acid precipitation and neutralization by means of an alkali according to well-known methods. For example, the method of NITSCHMANN and LEHMANN (11) may be used. The casein or $\alpha_{s1}$ casein, used as a starting product for obtaining the peptides according to the invention, may be obtained by standard methods well-known to one skilled in the art, from milk, from full caseins, from caseinates and total protein concentrates of milk, obtained for example according to the methods described by THOMSON (12) and MAUBOIS (13). For example, casein $\alpha_{s1}$ may be prepared by applying the method described by SANOGO et al. (14). This method is a fractionation method on DEAE-cellulose using a discontinuous gradient of calcium chloride as an eluent. It has the advantage of rapidly separating the whole of the caseins. It may advantageously be applied with, as an anion exchanger medium, DEAE-cellulose DE 52 [marketed by WHATMAN ltd, Springfeld, Great Britain] which is a pre-conditioned resin which does not require any acido-basic pre-cycle before its first use. The peptides may then be obtained by hydrolysis of casein with suitable enzymes. The peptides may then be concentrated or isolated by reverse phase high performance liquid chromatography (HPLC), by anion exchange high performance liquid chromatography or by size exclusion gel chromatography with a threshold of 1,000 Da or by membrane centrifugation and other membrane separation techniques (microfiltration, ultrafiltration, etc.).

Another object of the present invention is therefore a method for preparing peptides with an anxiolytic activity characterized in that it comprises the following steps:
enzymatic hydrolysis of casein;
isolation of at least one peptide selected from the peptides having the SEQ ID NOs. 1-3.

By isolation, is meant partial or total purification of the peptides according to the invention or simply enrichment of the obtained hydrolysates in peptides according to the invention. This enrichment may be carried out for example by fractionating the obtained hydrolysate. Alternatively, the hydrolysate obtained from $\alpha_{s1}$ casein containing at least one peptide according to the invention may be used directly for obtaining the pharmaceutical and food compositions according to the invention.

The peptides may also be obtained by peptide synthesis according to methods well-known to one skilled in the art, such as those described for example by MERRIFIELD (15).

The hydrolysates, the pharmaceutical and food compositions according to the invention may contain one or more peptides according to the invention. In a preferred embodiment, the invention relates to hydrolysates, pharmaceutical and food compositions containing the heptapeptide of SEQ ID NO. 1.

The invention will now be described in more detail by means of the non-limiting examples hereafter.

FIGURES

Figure 2:
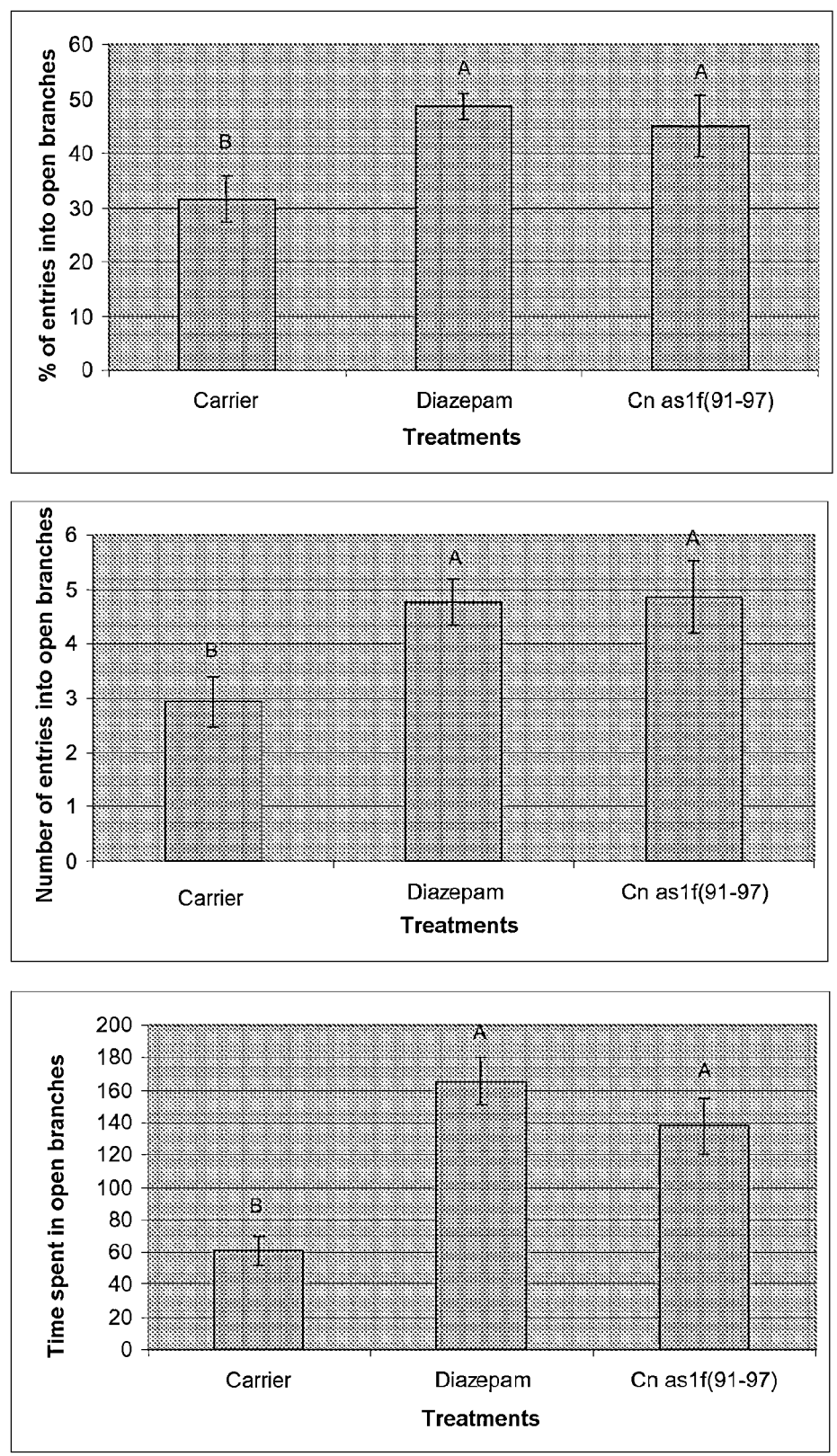
Figure 3:
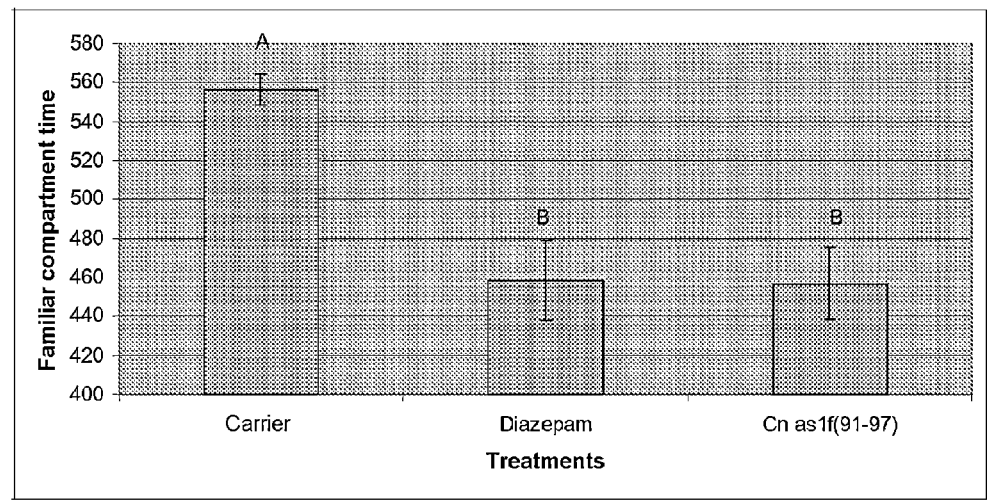
Figure 3:
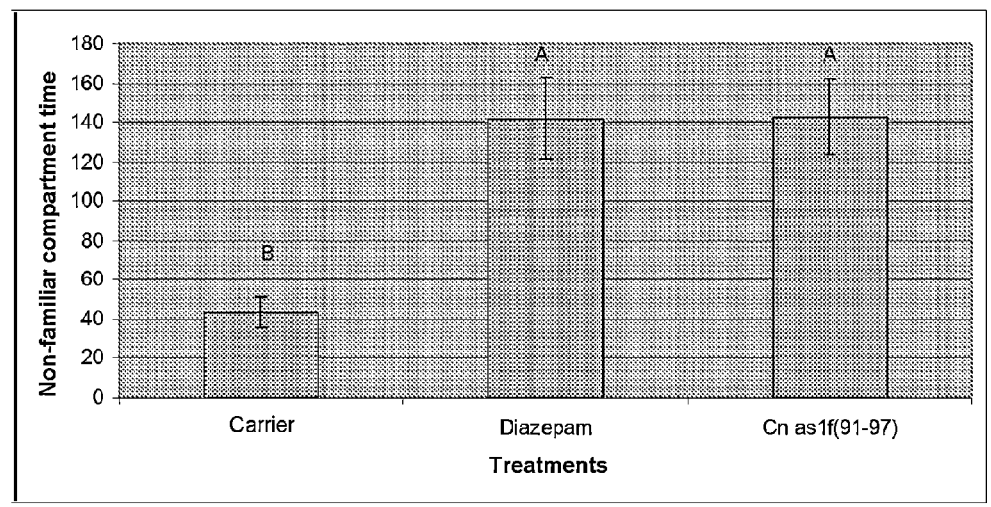

FIG. 1: conditioned defensive burial test
FIG. 2: elevated plus maze test
FIG. 3: the light/dark box test

EXAMPLES

1. Methods for Obtaining the Heptapeptide

Full casein is obtained from milk by acid precipitation and neutralization with an alkali according to well-known methods.

The heptapeptide having the amino acid sequence hereafter: Tyr-Leu-Gly-Tyr-Leu-Glu-Gln (SEQ. ID NO. 1) with a molecular mass of 884 Da, corresponds to the peptide 91-97 of $\alpha_{s1}$ casein. It may be obtained from $\alpha_{s1}$ casein by enzymatic hydrolysis, in particular by means of trypsin and then of pepsin. Hydrolysis by trypsin of $\alpha_{s1}$ casein releases various peptide fragments. The whole of the tryptic fragments undergo hydrolysis by pepsin A (EC 3.4.23.1) (originating from porcine gastric mucosa, with an activity of 3,200-4,500 units/mg of protein), in a ratio E/S=1/200 at acid pH, in a buffer and at an optimum temperature for the activity of the enzyme, for 240 minutes. This last hydrolysis releases new fragments including the heptapeptide 91-97 of $\alpha_{s1}$ casein. The heptapeptide may then be concentrated or isolated by reverse phase high performance liquid chromatography (HPLC), by anion exchange high performance liquid chromatography or by size exclusion filtration gel chromatography with a threshold of 1,000 Da or by membrane centrifugation or other membrane separation techniques (microfiltration, ultrafiltration, etc.).

2. Pharmaco-Behavioral Investigations in Wistar Rats 2.1. Conditioned Defensive Burial
2.1.1. Principle The conditioned defensive burial test was used for measuring the anxiety level in rats. Developed by PINEL and TREIT (16), this test is based on the innate tendency of rodents, placed in a familiar environment of burying any object perceived as being dangerous by projecting on the latter the litter present at ground level. The expression of the burial behavior by the animal is representative of its anxiety level: more it is anxious, more it buries. Thus, an electrode delivering a single low intensity shock causes the occurrence of burial behavior in rats and the administration of molecules with anxiolytic properties significantly reduces the duration of expression of this behavior.

2.1.2. Apparatuses

The test takes place in a Plexiglas box (44×28×18 cm), one of the walls of which has an orifice through which an electrode (7×2×0.5 cm) may be inserted. The bottom of the box is covered with a thick layer of sawdust (5 cm). The electrode is connected to a generator delivering a 1 mA intensity current when it is actuated by the experimenter. The whole of the experimentation is carried out in low intensity light.

2.1.3. Procedure

The experiment consists of habituation phase of 2 days followed by a test phase. During the habituation phase, the rats are placed 20 min daily in the test box, without the electrode, in order to accustom them to the experimental device. During the test phase, each rat is individually placed in the box which contains the electrode. When the animal touches the electrode in the first time, it receives a single shock. From this instant, its behavior is filmed for 5 min and behavioral variables are quantified.

2.1.4. Observations

The total burial time and the occurrence latency of the burial behavior after the shock are the most significant variables. A certain number of behaviors oriented towards the electrode and correlated with the anxiety level of the rat (approaches, escapes, contacts) are also counted. Finally, indicators of the activity level of the rat such as the number of upright standing postures are reported.

2.1.5. Treatments

The study dealt with 23 rats distributed into three groups:
- a control group (8 rats) having received 1 mL/kg of saline [NaCl 0.9% (m/v)],
- a group treated with diazepam (Valium®, Roche, Neuilly-sur-Seine, France) at the dose of 0.5 mg/kg (8 rats) used as a positive control,
- a group treated with the fragment 91-97 of $\alpha_{s1}$ casein, dissolved beforehand in a 0.9% (m/v) NaCl solution, at the dose of 0.5 mg/kg (7 rats).

The animals receive their respective treatments, via an intra-peritoneal route, half an hour before passing into the conditioned defensive burial test.

2.1.6. Results

The effect of the intra-peritoneal injection in Wistar rats of 1 mL/kg of 0.9% (m/v) NaCl (n=8), or of 0.5 mg/kg of diazepam (n=8) or of 0.5 mg/kg of the heptapeptide $CN\alpha_{s1}$-(f91-97) (n=7) on the burial duration of an aversive probe after a single 1 mA shock was studied by non-parametric variance analysis (Kruskall-Wallis) and comparisons of averages were conducted with the Mann-Whitney test (average a,b for each treatment are significantly different $p<0.05$, FIG. 1). The burial duration of animals treated with NaCl 0.9% (m/v) is significantly larger than that of animals treated with diazepam ($p<0.02$) and than that of animals treated by the fragment 91-97 of $\alpha_{s1}$ casein ($p<0.04$). No significant difference is seen between diazepam and the fragment 91-97 of $\alpha_{s1}$ casein. Accordingly, the fragment 91-97 of $\alpha_{s1}$ casein has an anxiolytic action in Wistar rats which acts in the same direction as that of diazepam.

2.2. Elevated Plus Maze 2.2.1. Principle

The elevated plus maze test allows the measurement of the density of exploratory behaviour in a new aversive situation [PELLOW et al., 1985 (17)]. The experiment exploits the conflict in rodents, between the fear of open spaces and the desire of exploring a new environment. The rat, placed at the centre of the device is forced to explore its environment. The open arms form an anxiogenic environment, whereas this is not the case of the closed arms. The number of entries in the whole of the arms, that relating to the open arms, the closed arms, the time spent in the open arms, the entry latency in the first open arm, form parameters which reflect the degree of anxiety of the animal.

2.2.2. Apparatuses

The elevated plus maze built in wood consists of four branches at 90° from each other. The two open branches (45×10 cm) and the two closed branches (45×10 cm; surrounded with wooden plates over a height of 40 cm) are positioned facing each other. The central square measures 10×10 cm. The open branches are illuminated by white light with an intensity of 500 lux. The elevated plus maze is located at 50 cm from the ground.

2.2.3. Procedure

The observations take place between 9.0 am and 11.0 am in order to minimize the influence of the circadian rhythm. After each passage in the elevated plus maze, the animal is placed for 10 min in an open field in order to stimulate its exploratory behavior. It is then placed in the central square of the elevated plus maze and observed for 5 min. The plus maze is washed with 95% (v/v) ethanol between two passages in order to eliminate the odors.

2.2.4. Treatments

The study dealt with 45 rats distributed in three groups:
- a control group (15 rats, having received 2 mL/kg of a solution containing 1% (v/v) of glycerol and 0.2% (v/v) of methyl cellulose (carrier),
- a group treated with diazepam (Valium®, Roche, Neuilly-sur-Seine, France) at the dose of 1 mg/kg suspended in the carrier (15 rats) being used as a positive control,
- a group treated with the fragment 91-97 of $\alpha_{s1}$ casein, dissolved beforehand in the carrier at the dose of 0.7 mg/kg (15 rats).

The animals receive their respective treatment via an intra-peritoneal route, half an hour before passing into the open field.

2.2.5. Results

The effect of the intra-peritoneal injection in Wistar rats of 2 mL/kg of a solution containing 1% (v/v) of glycerol and 0.2% (v/v) of methylcellulose (n=15) or of 1 mg/kg of diazepam (n=15) or of 0.7 mg/kg of the heptapeptide $CN\alpha_{s1}$-f (91-97) (n=15) on i) the percentage of entries into the open arms, (ii) on the number of entries into the open arms, (iii) on the time spent in the open arms was studied by non-parametric variance analysis (Kruskall-Wallis) and the comparisons of averages were conducted with the Mann-Whitney test (average A,B for each treatment are significantly different $p<0.05$, FIG. 2). The number of entries in the open arms, the percentage in the open arms, the time spent in the open arms of the animals treated with the carrier is significantly less than those of the animals treated with diazepam and than that of the animals treated with the fragment 91-97 of $\alpha_{s1}$ casein. No significant difference is seen between diazepam and the fragment 91-97 of the $\alpha_{s1}$ casein. The fragment 91-97 of the $\alpha_{s1}$ casein has in the elevated plus maze test in Wistar rats, an action similar to that exerted by diazepam.

2.3. Light/Dark Box 2.3.1. Principle

The light/dark tests are based on the innate aversion of rodents for intensively illuminated environments and on their spontaneous exploratory behavior in response to slight stress factors such as a new environment and light. The device of the light/dark box allows the study of the exploratory behavior of the rodent towards a non-familiar aversive compartment (intensively illuminated with white light) after habituation in a non-aversive compartment (dark) which then becomes familiar [BOURIN and HASCOËT, 2008 (18)]. Conventional anxiolytics may be detected by using this device.

2.3.2. Apparatuses and Procedure

The light/dark box measures 65×49×35 cm (h×w×l) and is separated into two identical compartments by a plate perforated with three doors of 8×8 cm. The floor is covered with sawdust. Each rat is placed for 24 h in the rear compartment of the box, the doors for communicating with the front compartment being inaccessible. The rear compartment thus becomes the familiar compartment. The animal is fed and hydrated ad libitum. On the day of the test, the rat after treatment is replaced in the familiar compartment and the doors communicating with the front compartment (non-familiar) are made accessible so that the animal may freely explore the environment. The non-familiar compartment is made aversive by white light illumination with an intensity of 1,500 lux. The animals are observed for 10 min and the time spent in each of the compartments is measured.

2.3.3. Treatments

The study deals with 36 rats distributed in three groups:
- a control group (12 rats, having received 2 mL/kg of a solution containing 1% (v/v) of glycerol and 0.2% (v/v) of methylcellulose (carrier), a group treated with diazepam (Valium®, Roche, Neuilly-sur-Seine, France) at the dose of 1 mg/kg suspended in the carrier (12 rats), being used as a positive control, a group treated with the fragment 91-97 of $\alpha_{s1}$ casein, dissolved beforehand in the carrier at the dose of 0.7 mg/kg (12 rats).

The animals receive their respective treatment via an intra-peritoneal route, half an hour before opening the communication between the familiar compartment and the non-familiar compartment.

2.3.4. Results

The effect of the intra-peritoneal injection in Wistar rats of 2 mL/kg of a solution containing 1% (v/v) glycerol and 0.2% (v/v) methylcellulose (n=12) or 1 mg/kg of diazepam (n=12) or 0.7 mg/kg of heptapeptide $CN\alpha_{s1}$-f(91-97) (n=12), on the time spent in the familiar compartment and on the time spent in the non-familiar compartment was studied by non-parametric variance analysis (Kruskall-Wallis) and the comparisons of averages were conducted with the Mann-Whitney test (averages A,B for each treatment are significantly different $p<0.05$, FIG. 3). The times spent in the aversive non-familiar compartment of the animals treated with the carrier are significantly less than those of the animals treated with diazepam and with that of the animals treated with the fragment 91-97 of $\alpha_{s1}$ casein. No significant difference is seen between diazepam and the fragment 91-97 of the $\alpha_{s1}$ casein. The fragment 91-97 of the $\alpha_{s1}$ casein shows an action similar to that of diazepam in the light/dark box test in Wistar rats.

BIBLIOGRAPHICAL REFERENCES (1) MERCIER, J. C., GROSCLAUDE, F., and RIBADEAU-DUMAS, B., 1971, Structure primaire de la caséine $\alpha_{s1}$ bovine. Séquence complète. Eur. J. Biochem., 23, 41-51.

(2) NAGAO, M., MAKI, M., SASAKI, R., and CHIBA, H., 1984, Isolation and sequence analysis of bovine $\alpha_{s1}$-casein cDNA clone. Agric. Biol. Chem., 48, 1663-1667.

(3) ZIOUDROU, C., STREATY, R. A., and KLEE, W. A., 1979, Opioid peptides derived from food proteins: the exorphins. J. Biol. Chem., 254, 2446-2449.

(4) LOUKAS, S., VAROUCHA, D., ZIOUDROU, C., STREATY, R. A., and KLEE, W. A., 1983, Opioid activities and structure of α-casein-derived exorphins. Biochemistry, 22, 4567-4573.

(5) MARUYAMA, S., and SUZUKI, H., 1982, A peptide inhibitor of angiotensin I converting enzyme in the tryptic hydrolysate of casein. Agric. Biol. Chem., 46, 1393-1394.

(6) MARUYAMA, S., MITACHI, H., AWAYA, J., KURONO, M., TOMIZUKA, N., and SUZUKI, H., 1987, Angiotensin I-converting enzyme inhibitory activity of the C-terminal hexapeptide of $\alpha_{s1}$-casein. Agric. Biol. Chem., 51, 2557-2561.

(7) MICLO, L., PERRIN, E., DRIOU, A., BOUDIER, J.-F., IUNG, C., and LINDEN G., 1995, Utilisation d'un décapeptide à activité de type benzodiazépine pour la préparation de médicaments et de compléments alimentaires. European Patent No. EP 0714910A1.

(8) MICLO, L., PERRIN, E., DRIOU, A., PAPADOPOULOS, V., BOUJRAD, N., VANDERESSE, R., BOUDIER, J.-F., DESOR, D., LINDEN, G., and GAILLARD, J.-L., 2001, Characterization of α-casozepine, a tryptic peptide from bovine $\alpha_{s1}$-casein with benzodiazepine-like activity. FASEB J. (Jun. 8, 2001) 10.1096/fj.00-0685fje.

(9) LECOUVEY, M., FROCHOT, C., MICLO, L., ORLEWSKI, P., DRIOU, A., LINDEN, A., GAILLARD, J.-L., MARRAUD, M., CLING, M.-T. and VANDERESSE R., 1997, Two dimensional $^1$H-NMR and CD structural analysis in a micellar medium of a bovin $\alpha_{s1}$-casein fragment having benzodiazepine-like properties. Eur. J. Biochem., 248, 872-878.

(10) FROCHOT, C. 1998, Étude d'un décapeptide à activité de type benzodiazépine issu d'une proéine du lait bovin. Thesis at the Institut Polytechnique de Lorraine (INPL).

(11) NITSCHMANN, H. S., and LEHMANN, W., 1947, Zum Problem der Labwirkung auf Casein, Helv. Chim. Acta, 130, 804.

(12) THOMSON, A. R, 1984, Recent developments in protein recovery and purification. J. Chem. Tech. Biotechnol., 34B, 190-198.

(13) MAUBOIS, J. L, 1984. Separation, extraction and fractionation of milk protein components. Lait, 64, 485-495.

(14) SANOGO, T., PAQUET, D., AUBERT, F., and LINDEN, G., 1989, Purification of $\alpha_{s1}$-casein by Fast Protein Liquid Chromatography. J. Dairy Sci., 72, 2242-2246.

(15) MERRIFIELD, R. B., 1963, Solid phase peptide synthesis. I. Synthesis of a tetrapeptide. J. Am. Chem. Soc., 85, 2149-2154.

(16) PINEL, J. P. J., and TREIT, D., 1978, Burying as a defensive response in rats. J. Comp. Physiol. Psychol. 92, 708-712.

(17) PELLOW, S., CHOPIN, P., FILE, S. E., and BRILEY, M., 1985, Validation of open closed arm entries in an elevated plus-maze as a measure of anxiety in the rat. J. Neurosci. Methods, 14, 149-167.

(18) BOURIN, M., and HASCOËT, M., 2003, The mouse light/dark box test. Eur. J. Pharmacol., 463, 55-65.

The invention claimed is:

1. An isolated peptide consisting of the amino acid sequence of SEQ ID NO:1 or SEQ ID NO:3.

2. A pharmaceutical composition comprising an effective amount of the peptide according to claim 1 and a suitable pharmaceutical carrier.

3. A food composition comprising an effective amount of the peptide according to claim 1.

4. A food supplement comprising an effective amount of the peptide according to claim 1 and alimentary supports of protein or carbohydrate nature.

5. A method for preparing a peptide comprising an anxiolytic activity comprising:

enzymatically hydrolyzing casein; and isolating at least one peptide consisting of the amino acid sequence SEQ ID NO: 1 or SEQ ID NO: 3.

6. A method for treating anxiety, a sleep disorder, or epilepsy in a mammal comprising administering to the mammal an effective amount of the peptide according to claim 1.

* * * * *

UNITED STATES PATENT AND TRADEMARK OFFICE
CERTIFICATE OF CORRECTION

PATENT NO. : 8,685,933 B2 Page 1 of 1
APPLICATION NO. : 12/519017
DATED : April 1, 2014
INVENTOR(S) : Balandras et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1326 days.

Signed and Sealed this

Twenty-ninth Day of September, 2015

Michelle K. Lee
*Director of the United States Patent and Trademark Office*